United States Patent
Fukuda

(10) Patent No.: US 9,911,064 B2
(45) Date of Patent: Mar. 6, 2018

(54) IMAGE DISPLAY DEVICE AND METHOD

(71) Applicant: FUJIFILM Corporation, Tokyo (JP)

(72) Inventor: Wataru Fukuda, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 222 days.

(21) Appl. No.: 14/846,082

(22) Filed: Sep. 4, 2015

(65) Prior Publication Data

US 2015/0379374 A1 Dec. 31, 2015

Related U.S. Application Data

(63) Continuation of application No. PCT/JP2014/054665, filed on Feb. 26, 2014.

(30) Foreign Application Priority Data

Mar. 28, 2013 (JP) .................................. 2013-067793

(51) Int. Cl.
*G06K 9/00* (2006.01)
*G06K 9/62* (2006.01)
(Continued)

(52) U.S. Cl.
CPC ............ *G06K 9/6202* (2013.01); *A61B 6/486* (2013.01); *A61B 6/5229* (2013.01); *G06T 3/0006* (2013.01); *G06T 7/0016* (2013.01); *G06T 7/337* (2017.01); *A61B 6/463* (2013.01); *A61B 6/502* (2013.01); *A61B 6/5205* (2013.01); *A61B 6/5235* (2013.01); *G06T 2207/10004* (2013.01);
(Continued)

(58) Field of Classification Search
None
See application file for complete search history.

(56) References Cited

U.S. PATENT DOCUMENTS

2005/0025365 A1 2/2005 Oosawa
2005/0285812 A1 12/2005 Shimayama et al.

FOREIGN PATENT DOCUMENTS

JP 2005-020719 A 1/2005
JP 2006-006435 A 1/2006
(Continued)

OTHER PUBLICATIONS

International Search Report issued in PCT/JP2014/054665, dated Mar. 25, 2014.
(Continued)

*Primary Examiner* — Amandeep Saini
(74) *Attorney, Agent, or Firm* — Birch, Stewart, Kolasch & Birch, LLP

(57) ABSTRACT

Provided is a technique for reducing the amount of calculation and storage costs when an alignment process and/or an image quality correction process is performed on a plurality of radiological images in order to perform comparative reading. A correction amount calculation unit 22 calculates a correction amount for matching the position and/or image quality of radiological images other than a reference radiological image among a plurality of radiological images including the same photographic subject with the position and/or image quality of the reference radiological image for each of the other radiological images. A storage processing unit 28 stores the correction amount for each of the other radiological images so as to be associated with the reference radiological image.

20 Claims, 5 Drawing Sheets

(51) Int. Cl.
*G06T 7/00* (2017.01)
*G06T 3/00* (2006.01)
*G06T 7/33* (2017.01)
*A61B 6/00* (2006.01)

(52) U.S. Cl.
CPC ............... *G06T 2207/10116* (2013.01); *G06T 2207/30068* (2013.01)

(56) References Cited

FOREIGN PATENT DOCUMENTS

| JP | 2011-125355 A | 6/2011 |
|----|---------------|--------|
| JP | 2011-125358 A | 6/2011 |
| JP | 2012-0235807 A | 12/2012 |

OTHER PUBLICATIONS

Written Opinion issued in PCT/JP2014/054665, dated Mar. 25, 2014.
Japanese Notice of Reasons for Rejection, dated Apr. 12, 2016, for corresponding Japanese Application No. 2013-067793, along with an English translation.

IMAGE DISPLAY DEVICE AND METHOD

CROSS REFERENCE TO RELATED APPLICATIONS

This application is a Continuation of PCT International Application No. PCT/JP2014/054665 filed on Feb. 26, 2014, which claims priority under 35 U.S.C § 119(a) to Japanese Patent Application No. 2013-067793 filed on Mar. 28, 2013, all of which are hereby expressly incorporated by reference into the present application.

BACKGROUND OF THE INVENTION

1. Field of the Invention

The present invention relates to an image display device and method which displays, for example, a radiological image of the breast.

2. Description of the Related Art

Comparative reading has been performed which displays a plurality of images of a photographic subject on a display device, such as a CRT or a liquid crystal display, and reads the images while comparing the images. For example, the current and past radiological images of the same part of a patient who is the photographic subject are displayed and comparative reading is performed for medical diagnosis to check the progress of a lesion or to find abnormalities in an early stage. A technique has been known which displays radiological images on a display device in order to facilitate the comparative reading. For example, JP2006-6435A and JP2012-235807A disclose a method which displays a plurality of radiological images for comparative reading on one screen so as to be switched. As such, when the radiological images to be compared are displayed so as to be switched, it is easy to check a changed part, which makes it possible to easily perform comparative reading. In addition, as a comparative reading method, a method has been used which calculates the difference between a plurality of radiological images. The calculation of the difference makes it easy to check a changed part. Therefore, it is possible to facilitate comparative reading.

However, the positions of the captured parts or imaging conditions during imaging are different from each other in a plurality of radiological images to be comparatively read or the radiological images are captured by different imaging devices. Therefore, in some cases, the position or image quality of the photographic subject included in the radiological images is different in the plurality of radiological images. In this case, it is necessary to perform a process of aligning the positions of the photographic subject included in the radiological images or to perform image processing for matching the image qualities of the plurality of radiological images, in order to effectively perform comparative reading which displays the plurality of radiological images so as to be switched. Therefore, the method disclosed in JP2006-6435A aligns the positions of a plurality of radiological images using, for example, affine transformation and makes the plurality of radiological images have the same brightness.

SUMMARY OF THE INVENTION

The above-mentioned comparative reading is used to compare the latest radiological image which is most recently captured with the past radiological image. The alignment process or the process of matching the image quality is performed using the latest radiological image as a reference. Therefore, the alignment process and/or an image quality correction process is performed for the past radiological image such that the position and/or image quality of the past radiological image is matched with the position and/or image quality of the latest radiological image.

The above-mentioned comparative reading is performed whenever a new radiological image is acquired. When the alignment process and the image quality correction process are performed for all of the past radiological images, using the new radiological image as a reference, whenever a new radiological image is acquired, an excessively large amount of calculation is required and a lot of time is required for the processes. In this case, all of the radiological images subjected to the alignment process and the image quality correction process may be stored. In this structure, when the correction amounts for the position and image quality of the latest radiological image and the position and image quality of any one of the radiological images are calculated, it is possible to correct the position and image quality of other radiological images. As a result, it is possible to reduce a calculation time.

However, when all of the past radiological images whose position and image quality have been corrected by performing the comparative reading are stored, the amount of data increases, which results in an increase in the costs of storing the radiological images.

The invention has been made in view of the above-mentioned problems and an object of the invention is to provide a technique which can reduce the amount of calculation and storage costs when an alignment process and/or an image quality correction process is performed on a plurality of radiological images for comparative reading.

According to the invention, there is provided an image display device that displays a plurality of radiological images including the same photographic subject for comparison. The image display device includes: a correction amount calculation unit for calculating a correction amount for matching the position and/or image quality of radiological images other than a reference radiological image among the plurality of radiological images with the position and/or image quality of the reference radiological image for each of the other radiological images; and a storage processing unit for storing the correction amount for each of the other radiological images so as to be associated with the reference radiological image.

In the image display device according to the invention, the correction amount calculation unit may calculate, as the correction amount for the position, at least one of correction amounts for rotation, scaling, and translation for aligning the position of the photographic subject included in the other radiological images with the position of the photographic subject included in the reference radiological image. The correction amount calculation unit may calculate, as the correction amount for the image quality, at least one of correction amounts for brightness, contrast, sharpness, and granularity for matching the image quality of the other radiological images with the image quality of the reference radiological image.

In the image display device according to the invention, the reference radiological image may be the latest radiological image among the plurality of radiological images.

The image display device according to the invention may further include an image processing unit for performing image processing for matching the position and/or image quality of the other radiological images with the position and/or image quality of the reference radiological image on the basis of the correction amount.

The image display device according to the invention may further include a display control unit for displaying the reference radiological image and the other corrected radiological images on display unit so as to be switched.

In the image display device according to the invention, when a new radiological image is acquired, the correction amount calculation unit may set the new radiological image as a new reference radiological image. The correction amount calculation unit may calculate a reference correction amount for matching the position and/or image quality of the reference radiological image before the new reference radiological image with the position and/or image quality of the new reference radiological image. The correction amount calculation unit may correct the correction amount for each of the other radiological images calculated before the calculation of a new correction amount, using the reference correction amount, to calculate the new correction amount including the reference correction amount and the corrected correction amount. The storage processing unit may store a new correction amount for each of new radiological images other than the new reference radiological image so as to be associated with the new reference radiological image.

According to the invention, there is provided an image display method that displays a plurality of radiological images including the same photographic subject for comparison. The image display method includes: a step of calculating a correction amount for matching the position and/or image quality of radiological images other than a reference radiological image among the plurality of radiological images with the position and/or image quality of the reference radiological image for each of the other radiological images; and a step of storing the correction amount for each of the other radiological images so as to be associated with the reference radiological image.

In addition, a program may be provided which causes a computer to perform the image display method according to the invention.

According to the invention, the correction amount for matching the position and/or image quality of the radiological images other than the reference radiological image among the plurality of radiological images with the position and/or image quality of the reference radiological image is calculated for each of the other radiological images and the correction amount for each of the other radiological images is stored so as to be associated with the reference radiological image. Therefore, when a new radiological image is acquired, the following process can be performed.

That is, the new radiological image is set as a new reference radiological image. The reference correction amount for matching the position and/or image quality of the reference radiological image before the new reference radiological image with the position and/or image quality of the new reference radiological image is calculated. Then, the correction amount for each of the other radiological images calculated before the calculation of a new correction amount is corrected on the basis of the reference correction amount to calculate the new correction amount including the reference correction amount and the corrected correction amount. A new correction amount for each of new radiological images other than the new reference radiological image is stored so as to be associated with the new reference radiological image. Therefore, according to the invention, it is not necessary to calculate for the correction amounts for all of the new reference radiological image and the other radiological images. As a result, it is possible to reduce the amount of calculation in a process for matching the position and/or image quality. In addition, only the correction amount is stored and the process for matching the position and/or image quality can be performed. Therefore, it is not necessary to store the radiological image whose position and/or image quality has been corrected. As a result, it is possible to reduce the amount of data stored and thus to reduce the costs of storing data.

DESCRIPTION OF THE PREFERRED EMBODIMENTS

Figure 1:
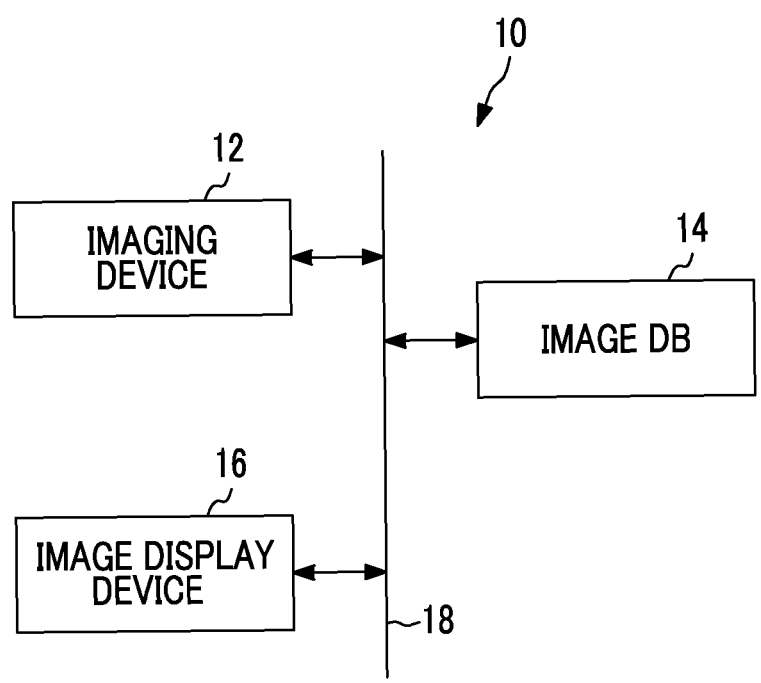
FIG. 1 is a block diagram schematically illustrating the structure of a medical image supporting system including an image display device according to an embodiment of the invention.

Hereinafter, embodiments of the invention will be described with reference to the drawings. FIG. 1 is a block diagram schematically illustrating the structure of a medical image supporting system to which an image display device according to an embodiment of the invention is applied. As illustrated in FIG. 1, a medical image supporting system 10 is installed in, for example, a medical facility and includes an imaging device 12 that captures an image of a photographic subject and acquires a radiological image of the photographic subject, an image database (image DB) 14 that stores the radiological image captured by the imaging device 12, and an image display device 16 that includes a high-resolution monitor (not illustrated) and is used to read the radiological image. These devices are connected to each other by a network 18. The image display device 16 is an image reading terminal used by the doctor.

In this embodiment, the imaging device 12 is a mammography device that captures the image of the breast of a patient who is the photographic subject. The mammography device captures the image of the breast of the patient and acquires a breast image which is a radiological image of the breast. The image data of the acquired breast image is stored in the image database 14. At that time, supplementary information, such as a patient name and an imaging date, is stored in the image database 14 so as to be associated with the image data of the breast image.

Figure 2:
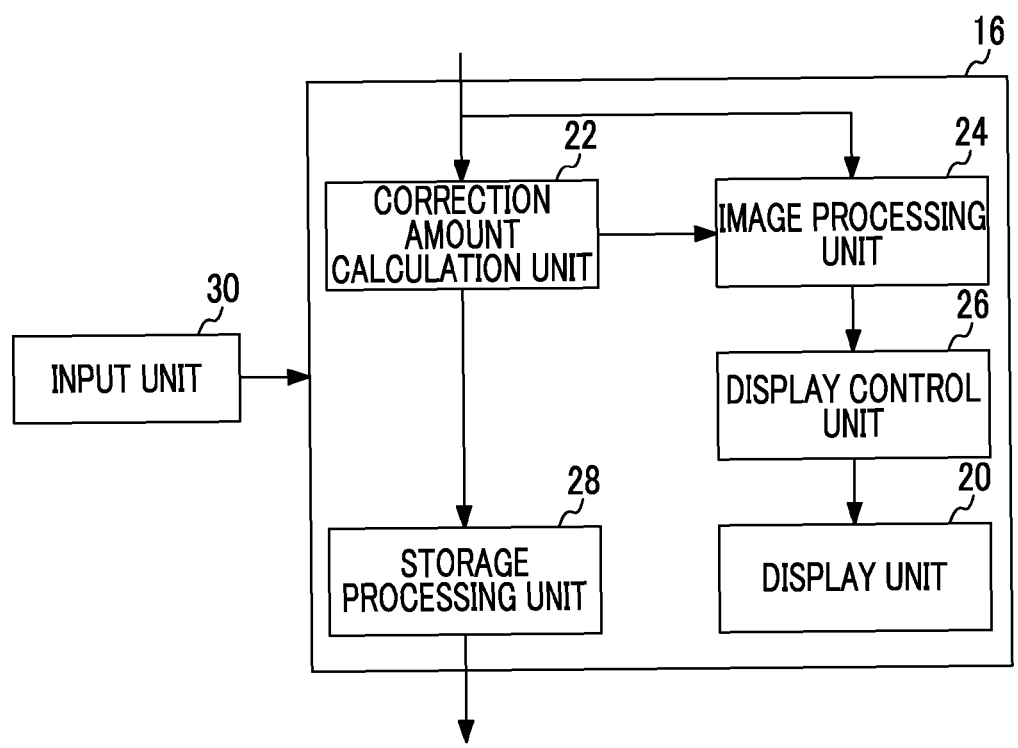
FIG. 2 is a block diagram schematically illustrating the structure of the image display device according to this embodiment.

FIG. 2 is a block diagram schematically illustrating the structure of the image display device. As illustrated in FIG. 2, the image display device 16 according to this embodiment includes a display unit 20, such as a CRT display or a liquid crystal display that displays images, a correction amount calculation unit 22 that calculates a correction amount for substantially aligning the positions of an anatomical structure in a plurality of breast images and for substantially matching the image quality of the plurality of breast images, on the basis of a plurality of input image data items indicating the breast images of the same patient captured at different dates and times, an image processing unit 24 that performs image processing including an alignment process and an image quality correction process for matching the position and image quality for at least one of the plurality of image data items, on the basis of the correction amount, a display control unit 26 that performs control such that the plurality of breast images subjected to the image processing are displayed on a screen of the display unit 20 so as to be switched on the basis of the plurality of image data items subjected to the image processing, a storage processing unit 28 that performs a process for storing the correction amount calculated by the correction amount calculation unit 22 in the image database 14, and an input unit 30 such as a mouse or a keyboard.

The display unit 20, the correction amount calculation unit 22, the image processing unit 24, the display control unit 26, the storage processing unit 28, and the input unit 30 can be configured by a computer system such as a general personal computer.

It is assumed that the plurality of the breast images with different imaging dates and times which are used in this embodiment are the latest breast image M0 at the present time and n past breast images M1 to Mn of the same patient. In addition, any of the left and right breasts may be an imaging target.

The correction amount calculation unit 22 calculates a correction amount for matching the position and image quality of the past breast images M1 to Mn with the position and image quality of the latest breast image M0. The latest breast image M0 corresponds to a reference radiological image and the past breast images M1 to Mn correspond to the other radiological images. First, the calculation of the correction amount for the position will be described. The correction amount for the position is used for an alignment process for aligning the position of the past breast images M1 to Mn with the position of the latest breast image M0 such that an anatomical structure in the past breast images M1 to Mn is aligned with an anatomical structure in the latest breast image M0.

Here, a method using affine transformation disclosed in JP2006-6435A, JP1995-262346A (JP-H07-262346A), and JP2010-188003A is given as an example of the alignment method. The affine transformation is a method which calculates a plurality of corresponding points between images, calculates parameters for rotation, scaling, and translation for aligning the corresponding points between the images, and converts one image on the basis of the parameters so as to be aligned with the other images. In this embodiment, the correction amount calculation unit 22 calculates, as position correction amounts P1 to Pn, affine transformation parameters for aligning the position of each of the past breast images M1 to Mn with the position of the latest breast image M0, that is, parameters for rotation, scaling, and translation.

In addition, the mammary gland may be extracted from the breast image by the method disclosed in JP2002-125961A on the basis of the brightness of the breast image, and parameters for rotation, scaling, and translation for aligning the position of each of the past breast images M1 to Mn with the position of the latest breast image M0 such that the shape and the position of the center of gravity of the mammary gland are matched may be calculated as the position correction amount.

In addition, the methods disclosed in JP2001-325584A and JP2002-324238A may be used. Specifically, parameters for rotation, scaling, and translation for aligning the position of each of the past breast images M1 to Mn with the position of the latest breast image M0 such that a specific structure (for example, a nipple in the breast image) is aligned may be calculated as the position correction amounts.

The method disclosed in JP2002-65613A may be used. Specifically, a method may be used which recognizes the position of the breast in the image using a known recognition technique and performs a warping process for one image such that the position of a pectoral muscle and the position of the nipple of the breast are aligned with each other between two images. In this case, parameters for the warping process may be calculated as the position correction amounts.

Next, a correction amount for image quality will be described. Here, the reason why image quality is corrected is that, when there is a variation in image quality between images, it is difficult for the observer to see the images during image switching display, which will be described below. The correction amount for image quality is used for image processing for correcting the quality of the past breast images M1 to Mn such that the quality of the past breast images M1 to Mn is matched with the quality of the latest breast image M0. In this embodiment, specifically, correction amounts for brightness, contrast, sharpness, and granularity are calculated as image quality correction amounts G1 to Gn.

For example, the correction amount calculation unit 22 calculates, as a brightness correction amount, a correction amount for making the maximum and minimum values of the pixel values of the past breast images M1 to Mn equal to the maximum and minimum values of the pixel value of the latest breast image M0, respectively. In addition, the correction amount calculation unit 22 calculates, as a contrast correction amount, a correction amount for making the contrast of the past breast images M1 to Mn equal to the contrast of the pixel value of the latest breast image M0. In addition, a difference between the maximum value and the minimum value of the pixel values can be used as the contrast. In this case, the contrast correction amount is the gradient of a gamma curve for changing the gradation of the breast image.

The correction amount calculation unit 22 performs a frequency analysis process for the latest breast image M0 and the past breast images M1 to Mn to calculate the frequency band response of each breast image as sharpness characteristics and calculates, as a sharpness correction amount, a correction amount for making the sharpness of the past breast images M1 to Mn equal to the sharpness of the latest breast image M0.

In addition, the correction amount calculation unit 22 performs frequency analysis to calculate frequency band responses included in the latest breast image M0 and the past breast images M1 to Mn as granularity characteristics and calculates, as a granularity correction amount, a correction amount for matching the frequency band response of the granularity of the past breast images M1 to Mn with the frequency band response of the granularity of the latest breast image M0.

The correction amount calculation unit 22 provides the position correction amounts P1 to Pn and the image quality correction amounts G1 to Gn, which have been respectively calculated for the past breast images M1 to Mn, as position and image quality correction amounts H1 to Hn to the image processing unit 24 and the storage processing unit 28.

The image processing unit 24 performs image processing for matching the position and image quality of the past breast images M1 to Mn with the position and image quality of the latest breast image M0 for the past breast images M1 to Mn. That is, the image processing unit 24 performs an alignment process for aligning the position of the past breast images M1 to Mn with the position of the latest breast image M0, using the position correction amounts P1 to Pn among the correction amounts H1 to Hn calculated by the correction amount calculation unit 22. In addition, the image processing unit 24 performs an image quality correction process for making the concentration, contrast, sharpness, and granularity of the past breast images M1 to Mn equal to the concentration, contrast, sharpness, and granularity of the latest breast image M0, using the image quality correction amounts G1 to Gn.

The display control unit 26 controls the display unit 20 such that a plurality of breast images subjected to image processing are displayed so as to be switched, in response to an instruction to switch the breast images displayed on the screen which is input from the input unit 30 by an operator. At the time of switching, for example, a display speed can be in the range of 1 to 5 frames per second.

The storage processing unit 28 performs a process of storing the correction amounts M1 to Mn calculated by the correction amount calculation unit 22 in the image database 14 so as to be associated with a reference breast image which is a reference for matching the position and image quality. In this embodiment, the reference breast image is the latest breast image M0.

Figure 3:
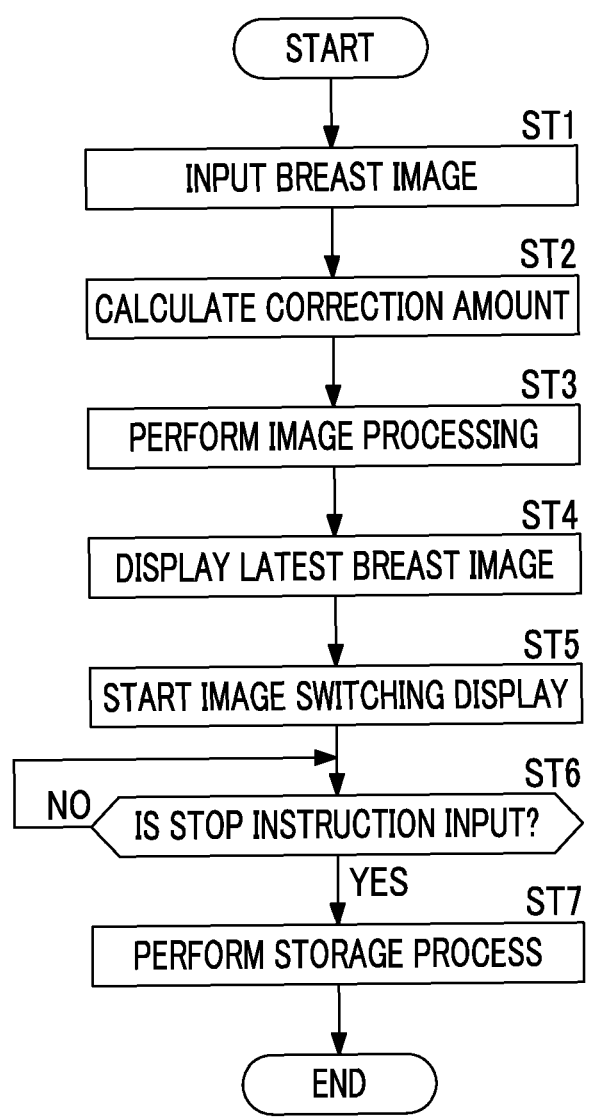
FIG. 3 is a flowchart illustrating a process performed in this embodiment.

Next, a process performed in this embodiment will be described. FIG. 3 is a flowchart illustrating the process performed in this embodiment. First, a plurality of breast images including the latest breast image M0 and the past breast images M1 to Mn of the same patient are read from the image database 14 and are then input to the image display device 16 (Step ST1).

When the breast images M0 and M1 to Mn are input, the correction amount calculation unit 22 calculates the correction amounts H1 to Hn for matching the position and image quality of the past breast images M1 to Mn with the position and image quality of the latest breast image M0 (Step ST2). The correction amounts H1 to Hn are supplied to the image processing unit 24 and the storage processing unit 28. The image processing unit 24 performs image processing for matching the position and image quality of the past breast images M1 to Mn with the position and image quality of the latest breast image M0 on the basis of the correction amounts H1 to Hn (Step ST3).

After the image processing, the display control unit 26 displays any one of the breast images M0 and M1 to Mn on the screen of the display unit 20 (Step ST4). In this embodiment, it is assumed that the latest breast image M0 is displayed first.

Then, when the operator uses the input unit 30 to input an image switching display start instruction, the display control unit 26 starts to display the breast images M0 and M1 to Mn so as to be switched (Step ST5). That is, the display control unit 26 displays the breast images M0 and M1 to Mn on the screen of the display unit 20 so as to be repeatedly switched in time series (for example, in reverse chronological order of the imaging date and time) at a predetermined display speed (for example, about 1 to 5 frames per second). Therefore, the latest breast image M0 and the past breast images M1 to Mn are displayed so as to be switched.

Before and while the images are displayed so as to be switched, for example, the display speed may be changed on the basis of information input from the input unit 30. In this case, the operator can adjust the display speed to a desired value at which the operator easily observes the images.

Then, the display control unit 26 starts to monitor whether an image switching display stop instruction is input from the input unit 30 (Step ST6). When the monitoring result in Step ST6 is "Yes", the display control unit 26 ends the image switching display.

Then, the storage processing unit 28 performs a process of storing the correction amounts H1 to Hn corresponding to the past breast images M1 to Mn, which have been calculated by the correction amount calculation unit 22, in the image database 14 so as to be associated with the latest breast image M0 (Step ST7) and ends the process. The storage process stores the latest breast image M0 and the correction amounts H1 to Hn in the image database 14 such that the latest breast image M0 is inseparable from the correction amounts H1 to Hn corresponding to the past breast images M1 to Mn. For example, the following processes are used as the storage process: a process of describing the correction amounts H1 to Hn in a header of the latest breast image M0; a process of associating the file name of the correction amounts H1 to Hn with the file name of the latest breast image M0; and a process of storing a file of the correction amounts H1 to Hn in the same folder as a file of the latest breast image M0.

Figure 4:
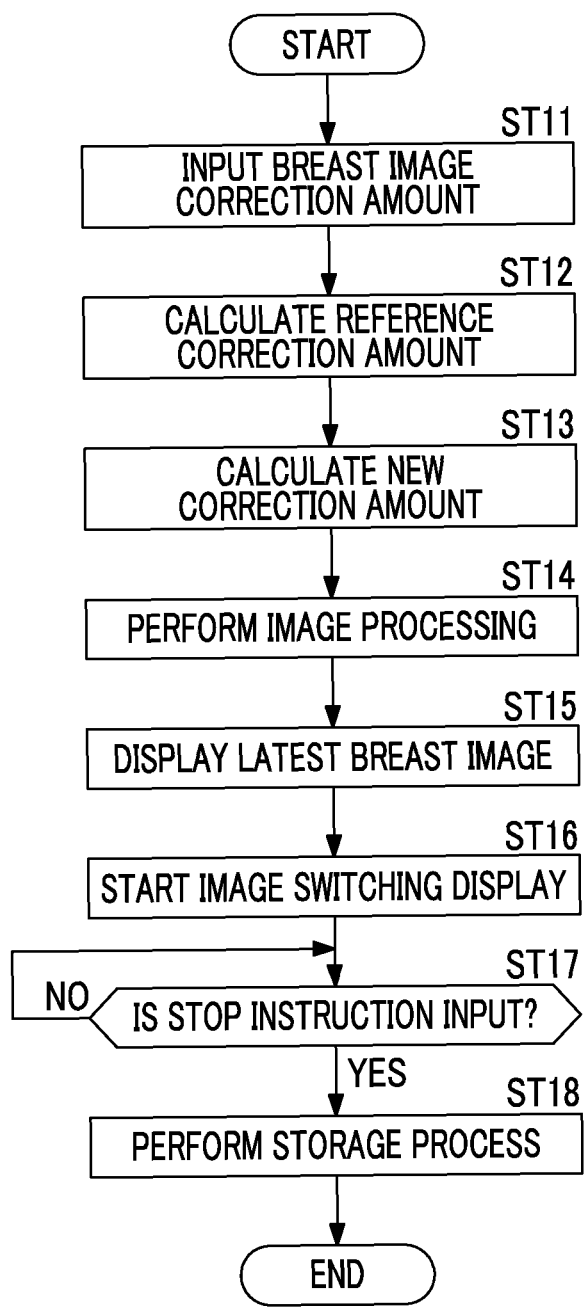
FIG. 4 is a flowchart illustrating a process when a new image of the breast is captured.

Next, a process when a new image of the breast of the same patient is captured will be described. FIG. 4 is a flowchart illustrating a process performed by the image display device 16 when a new image of the breast of the same patient is captured. When the latest breast image (which is represented by "Mnew") of the breast is newly captured by the imaging device 12, the latest breast image Mnew is stored in the image database 14. During image switching display, the latest breast image Mnew and the breast images M0 and M1 to Mn of the same patient are read from the image database 14 and are then input to the image display device 16 (Step ST11). At that time, the correction amounts M1 to Mn associated with the breast image M0 are also input to the image display device 16.

First, the correction amount calculation unit 22 calculates a correction amount for matching the position and image quality of the breast image M0 with the position and image quality of the latest breast image Mnew, using the latest breast image Mnew and the previous latest breast image M0. In addition, the calculated correction amount is a reference (hereinafter, referred to as a "reference correction amount H0") for calculating a correction amount for matching the position and image quality of the latest breast image Mnew with the position and image quality of the breast images M1 to Mn, which will be described below (calculation of the reference correction amount, Step ST12).

Figure 5:
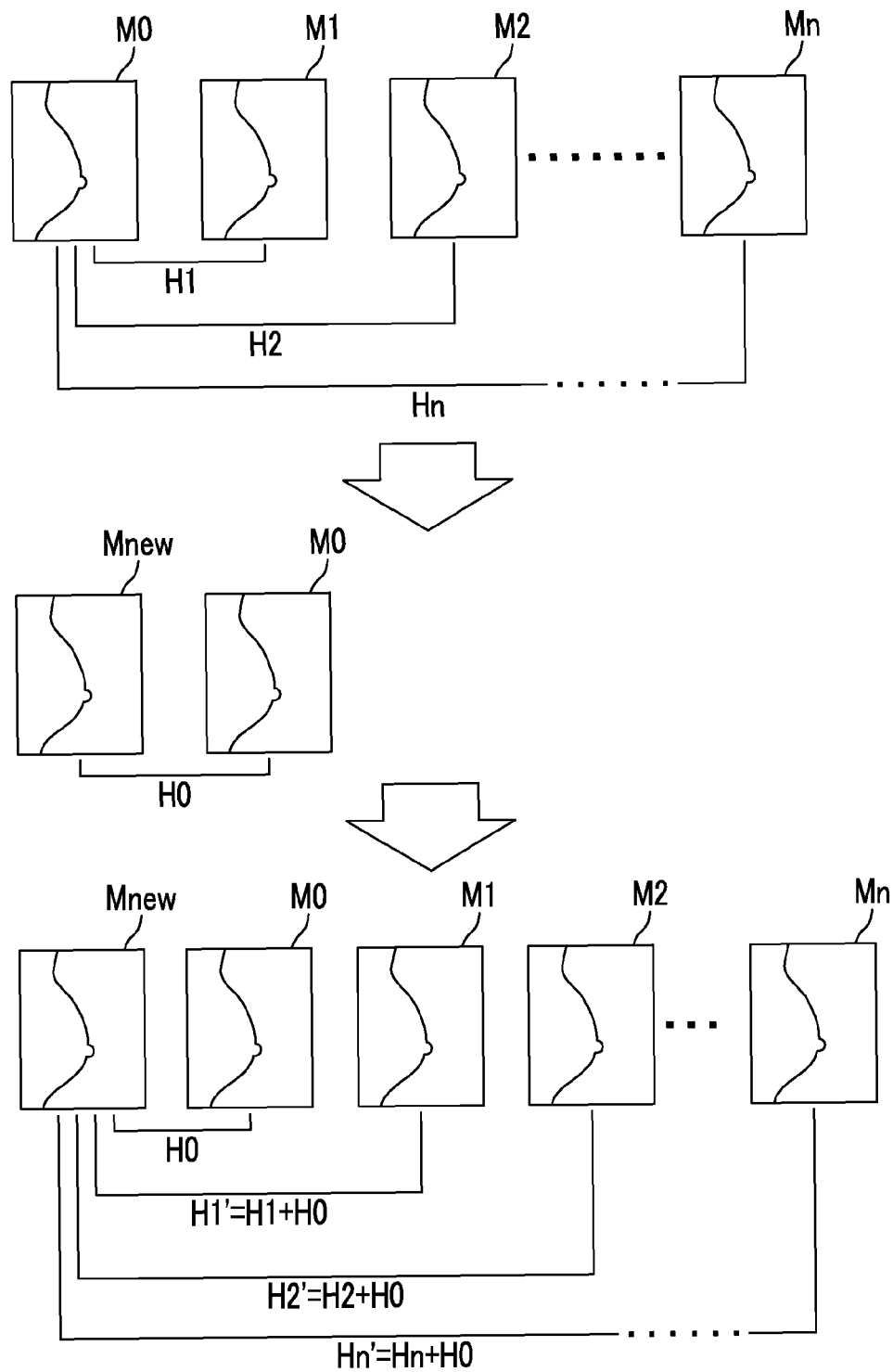
FIG. 5 is a diagram illustrating the calculation of a new correction amount.

Then, the correction amount calculation unit 22 corrects the correction amounts H1 to Hn associated with the breast image M0 using the reference correction amount H0 and calculates new correction amounts H1' to Hn' (Step ST13). FIG. 5 is a diagram illustrating the calculation of the new correction amounts H1' to Hn'. As illustrated in FIG. 5, the breast image M0 is associated with the correction amounts H1 to Hn for the breast images M1 to Mn captured earlier than the breast image M0. Here, the correction amount H1 is used to match the position and image quality of the breast image H1 with the position and image quality of the breast image M0 and the correction amount H2 is used to match the position and image quality of the breast image H2 with the position and image quality of the breast image M0.

The reference correction amount H0 is a correction amount for matching the position and image quality of the breast image M0 with the position and image quality of the latest breast image Mnew. Therefore, the correction amounts H1 to Hn are corrected using the reference correction amount H0 to calculate new correction amounts H1' to Hn' for matching the position and image quality of the past breast images M1 to Mn with the position and image quality of the latest breast image Mnew. Specifically, a predetermined operation can be performed using (combining) the correction amounts H1 to Hn and the reference correction amount H0 to calculate the new correction amounts H1' to Hn'. For example, as illustrated in FIG. 5, the reference correction amount H0 is added to the correction amounts H1 to Hn to calculate the new correction amounts H1' to Hn'. As such, the correction amount calculation unit 22 corrects the correction amounts H1 to Hn using the reference correction amount H0 to calculate the new correction amounts H1' to Hn'.

Then, the image processing unit 24 performs image processing for matching the position and image quality of the breast images M0 and M1 to Mn with the position and image quality of the latest breast image Mnew, on the basis of the reference correction amount H0 and the new correction amounts H1' to Hn' (Step ST14). After the image processing, the display control unit 26 displays the latest breast image Mnew on the screen of the display unit 20 (Step ST15). Then, when the operator uses the input unit 30 to input an image switching display start instruction, the display control unit 26 starts to display the breast images Mnew, M0, and M1 to Mn so as to be switched (Step ST16). Then, the display control unit 26 starts to monitor whether an image switching display stop instruction is input from the input unit 30 (Step ST17). When the monitoring result in Step ST17 is "Yes", the display control unit 26 ends the image switching display.

Then, the storage processing unit 28 performs a process of storing the reference correction amount H0 and the new correction amounts H1' to Hn' calculated by the correction amount calculation unit 22 in the image database 14 so as to be associated with the latest breast image Mnew (Step ST18) and ends the process. In addition, the correction amounts H1 to Hn associated with the breast image M0 may be stored in the image database 14 so as to be associated with the breast image M0 or may be deleted in order to reduce the amount of stored data.

As such, in this embodiment, the correction amounts H1 to Hn for matching the position and image quality of the past breast images M1 to Mn with the position and image quality of the latest breast image M0 are calculated for each of the past breast images M1 to Mn and the correction amounts H1 to Hn are stored so as to be associated with the latest breast image M0. Therefore, when the new breast image Mnew is acquired, the reference correction amount H0 for matching the position and image quality of the breast image M0, which follows the new breast image Mnew in reverse chronological order of the imaging time, with the position and image quality of the latest breast image Mnew can be calculated. Then, the correction amounts H1 to Hn for the past breast images M1 to Mn can be corrected using the reference correction amount G0 to calculate the new correction amounts H1' to Hn'. Then, the reference correction amount H0 and the new correction amounts H1' to Hn' can be stored so as to be associated with the new breast image Mnew. Therefore, when the new breast image Mnew is input, it is not necessary to calculate a correction amount for all of the new breast image Mnew and the other breast images M0 and M1 to Mn. As a result, it is possible to reduce the amount of calculation in a process of matching the position and image quality. In addition, since the process of matching the position and image quality can be performed using the correction amount, it is not necessary to store the breast image whose position and image quality have been corrected (only the correction amount is stored). Therefore, it is possible to reduce the amount of data stored and to reduce the costs of storing data in the image database 14.

In the above-described embodiment, the parameters for rotation, scaling, and translation are calculated as the position correction amounts P1 to Pn. However, parameters for at least one of the rotation, scaling, and translation may be calculated as the position correction amounts P1 to Pn.

In the above-described embodiment, the correction amounts for brightness, contrast, sharpness, and granularity are calculated for the image quality correction amounts G1 to Gn. However, the correction amount for at least one of the brightness, contrast, sharpness, and granularity may be calculated for the image quality correction amounts G1 to Gn.

In the above-described embodiment, the correction amounts H1 to Hn for matching the position and image quality of the past breast images with the position and image quality of the breast image M0 are calculated. However, the correction amounts H1 to Hn for matching at least one of the position and the image quality (the position and/or the image quality) may be calculated. That is, any of the position correction amounts P1 to Pn and the image quality correction amounts G1 to Gn may be calculated.

In the above-described embodiment, the correction amount may be calculated before a plurality of the breast images with different imaging dates and times are displayed so as to be switched. In this case, during image switching display, it is not necessary to calculate the correction amount and it is possible to reduce the amount of time required to start image switching display.

In the above-described embodiment, the breast is the photographic subject. However, the photographic subject is not limited to the breast. For example, the photographic subject may be an arbitrary part of the human body, such as the chest, the abdomen, the head, or the limbs.

The invention is not limited to the above-mentioned examples and various modifications and changes of the invention can be made without departing from the scope and spirit of the invention.

EXPLANATION OF REFERENCES

10: medical image supporting system
12: imaging device
14: image database
16: image display device
20: display unit
22: correction amount calculation unit
24: image processing unit
26: display control unit
28: storage processing unit
30: input unit

What is claimed is:

1. An image display that displays a plurality of radiological images including the same photographic subject for comparison, comprising:
   a processor configured to:
   calculate a correction amount for matching the position or image quality of radiological images other than a reference radiological image among the plurality of radiological images with the position and/or image quality of the reference radiological image for each of the other radiological images;
   store the correction amount for each of the other radiological images so as to be associated with the reference radiological image; and generate an image based on the calculated correction amount.

2. The image display according to claim 1,
wherein the processor calculates, as the correction amount for the position, at least one of correction amounts for rotation, scaling, and translation for aligning the position of the photographic subject included in the other radiological images with the position of the photographic subject included in the reference radiological image, and
the processor calculates, as the correction amount for the image quality, at least one of correction amounts for brightness, contrast, sharpness, and granularity for matching the image quality of the other radiological images with the image quality of the reference radiological image.

3. The image display according to claim 1,
wherein the reference radiological image is the latest radiological image among the plurality of radiological images.

4. The image display according to claim 2,
wherein the reference radiological image is the latest radiological image among the plurality of radiological images.

5. The image display according to claim 1, wherein the processor further performs image processing for matching the position or image quality of the other radiological images with the position or image quality of the reference radiological image on the basis of the correction amount.

6. The image display according to claim 2, wherein the processor further performs image processing for matching the position or image quality of the other radiological images with the position or image quality of the reference radiological image on the basis of the correction amount.

7. The image display according to claim 3, wherein the processor further performs image processing for matching the position or image quality of the other radiological images with the position or image quality of the reference radiological image on the basis of the correction amount.

8. The image display according to claim 4, wherein the processor further performs image processing for matching the position or image quality of the other radiological images with the position or image quality of the reference radiological image on the basis of the correction amount.

9. The image display according to claim 5, wherein the processor further displays the reference radiological image and the other corrected radiological images on display unit so as to be switched.

10. The image display according to claim 6, wherein the processor further displays the reference radiological image and the other corrected radiological images on display unit so as to be switched.

11. The image display according to claim 7, wherein the processor further displays the reference radiological image and the other corrected radiological images on display unit so as to be switched.

12. The image display according to claim 8, wherein the processor further displays the reference radiological image and the other corrected radiological images on display unit so as to be switched.

13. The image display according to claim 1,
wherein, when a new radiological image is acquired, the processor sets the new radiological image as a new reference radiological image,
the processor calculates a reference correction amount for matching the position or image quality of the reference radiological image before the new reference radiological image with the position or image quality of the new reference radiological image,
the processor corrects the correction amount for each of the other radiological images calculated before the calculation of a new correction amount, using the reference correction amount, to calculate the new correction amount including the reference correction amount and the corrected correction amount, and
the processor stores a new correction amount for each of new radiological images other than the new reference radiological image so as to be associated with the new reference radiological image.

14. The image display according to claim 2,
wherein, when a new radiological image is acquired, the processor sets the new radiological image as a new reference radiological image,
the processor calculates a reference correction amount for matching the position or image quality of the reference radiological image before the new reference radiological image with the position or image quality of the new reference radiological image,
the processor corrects the correction amount for each of the other radiological images calculated before the calculation of a new correction amount, using the reference correction amount, to calculate the new correction amount including the reference correction amount and the corrected correction amount, and
the processor stores a new correction amount for each of new radiological images other than the new reference radiological image so as to be associated with the new reference radiological image.

15. The image display according to claim 3,
wherein, when a new radiological image is acquired, the processor sets the new radiological image as a new reference radiological image,
the processor calculates a reference correction amount for matching the position or image quality of the reference radiological image before the new reference radiological image with the position or image quality of the new reference radiological image,
the processor corrects the correction amount for each of the other radiological images calculated before the calculation of a new correction amount, using the reference correction amount, to calculate the new correction amount including the reference correction amount and the corrected correction amount, and
the processor stores a new correction amount for each of new radiological images other than the new reference radiological image so as to be associated with the new reference radiological image.

16. The image display according to claim 4,
wherein, when a new radiological image is acquired, the processor sets the new radiological image as a new reference radiological image,
the processor calculates a reference correction amount for matching the position or image quality of the reference radiological image before the new reference radiological image with the position or image quality of the new reference radiological image,
the processor corrects the correction amount for each of the other radiological images calculated before the calculation of a new correction amount, using the reference correction amount, to calculate the new correction amount including the reference correction amount and the corrected correction amount, and
the processor stores a new correction amount for each of new radiological images other than the new reference radiological image so as to be associated with the new reference radiological image.

17. The image display according to claim 5,
wherein, when a new radiological image is acquired, the processor sets the new radiological image as a new reference radiological image, the processor calculates a reference correction amount for matching the position or image quality of the reference radiological image before the new reference radiological image with the position or image quality of the new reference radiological image, the processor corrects the correction amount for each of the other radiological images calculated before the calculation of a new correction amount, using the reference correction amount, to calculate the new correction amount including the reference correction amount and the corrected correction amount, and the processor stores a new correction amount for each of new radiological images other than the new reference radiological image so as to be associated with the new reference radiological image.

18. The image display according to claim 6,
wherein, when a new radiological image is acquired, the processor sets the new radiological image as a new reference radiological image, the processor calculates a reference correction amount for matching the position or image quality of the reference radiological image before the new reference radiological image with the position or image quality of the new reference radiological image, the processor corrects the correction amount for each of the other radiological images calculated before the calculation of a new correction amount, using the reference correction amount, to calculate the new correction amount including the reference correction amount and the corrected correction amount, and the processor stores a new correction amount for each of new radiological images other than the new reference radiological image so as to be associated with the new reference radiological image.

19. The image display according to claim 7,
wherein, when a new radiological image is acquired, the processor sets the new radiological image as a new reference radiological image, the processor calculates a reference correction amount for matching the position or image quality of the reference radiological image before the new reference radiological image with the position or image quality of the new reference radiological image, the processor corrects the correction amount for each of the other radiological images calculated before the calculation of a new correction amount, using the reference correction amount, to calculate the new correction amount including the reference correction amount and the corrected correction amount, and the processor stores a new correction amount for each of new radiological images other than the new reference radiological image so as to be associated with the new reference radiological image.

20. An image display method that displays a plurality of radiological images including the same photographic subject for comparison, using the image display according to claim 1, comprising:

a step of calculating a correction amount for matching the position or image quality of radiological images other than a reference radiological image among the plurality of radiological images with the position or image quality of the reference radiological image for each of the other radiological images; and a step of storing the correction amount for each of the other radiological images so as to be associated with the reference radiological image.

\* \* \* \* \*